(12) United States Patent
Tralshawala et al.

(10) Patent No.: US 8,120,522 B2
(45) Date of Patent: Feb. 21, 2012

(54) SYSTEM AND METHOD FOR INSPECTING A WIND TURBINE BLADE

(75) Inventors: Nilesh Tralshawala, Rexford, NY (US); Waseem Ibrahim Faidi, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/956,212

(22) Filed: Nov. 30, 2010

(65) Prior Publication Data

US 2011/0090110 A1 Apr. 21, 2011

(51) Int. Cl.
*G01S 13/89* (2006.01)
*G01S 13/90* (2006.01)
*G01S 13/32* (2006.01)
*G01S 13/00* (2006.01)

(52) U.S. Cl. .................... 342/25 F; 342/25 R; 342/25 A; 342/118; 342/128; 342/175; 342/176; 342/179; 342/195; 415/118; 415/232; 416/61

(58) Field of Classification Search .............. 342/21, 342/22, 27, 28, 25 R–25 F, 118, 128–133, 342/165, 173–176, 179, 192–197; 324/71.1, 324/600, 629, 637, 642, 639, 649, 654, 655; 415/118, 232; 416/61; 702/127, 182–186; 429/400, 428, 443; 73/570, 584, 596, 632, 73/642, 649, 658, 660; 382/100, 141, 152
See application file for complete search history.

(56) References Cited

U.S. PATENT DOCUMENTS

| | | | | | |
|---|---|---|---|---|---|
| 3,478,353 | A | * | 11/1969 | Adams, Jr. | 416/61 |
| 3,810,005 | A | * | 5/1974 | Bennion et al. | 324/639 |
| 3,922,907 | A | * | 12/1975 | Hurwitz et al. | 73/642 |
| 4,413,519 | A | * | 11/1983 | Bannister et al. | 342/118 |
| 4,507,658 | A | * | 3/1985 | Keating | 342/118 |
| 5,479,826 | A | * | 1/1996 | Twerdochlib et al. | 324/642 |
| 5,748,003 | A | * | 5/1998 | Zoughi et al. | 324/637 |
| 5,818,242 | A | * | 10/1998 | Grzybowski et al. | 324/642 |
| 6,448,924 | B1 | * | 9/2002 | Hafer, Jr. | 342/28 |
| 6,881,507 | B2 | * | 4/2005 | Milacic | 429/443 |
| 6,966,754 | B2 | | 11/2005 | Wobben | |
| 6,968,730 | B2 | * | 11/2005 | Schafrik et al. | 324/637 |
| 7,019,537 | B2 | * | 3/2006 | Hazel et al. | 324/639 |
| 7,083,384 | B2 | * | 8/2006 | Bosselmann et al. | 416/61 |
| 7,095,221 | B2 | * | 8/2006 | Bosselmann et al. | 324/71.1 |
| 7,432,505 | B2 | * | 10/2008 | Brummel | 382/152 |
| 7,554,324 | B2 | * | 6/2009 | Gualtieri | 324/655 |
| 7,825,669 | B2 | * | 11/2010 | Parsons et al. | 324/637 |
| 7,889,119 | B2 | * | 2/2011 | Evers et al. | 342/118 |
| 2006/0181285 | A1 | * | 8/2006 | Friedman et al. | 324/600 |
| 2007/0132461 | A1 | * | 6/2007 | Holmquist et al. | 324/642 |
| 2010/0253569 | A1 | * | 10/2010 | Stiesdal | 342/118 |

FOREIGN PATENT DOCUMENTS

JP 11295274 A 10/1999
WO 2010032134 A2 3/2010

* cited by examiner

*Primary Examiner* — Bernarr Gregory
(74) *Attorney, Agent, or Firm* — Ann M. Agosti

(57) ABSTRACT

A wind turbine blade inspection system includes a frequency modulated continuous wave radar system configured to be movable with respect to a wind turbine blade while transmitting reference microwave signals and receiving reflected microwave signals and a processor configured for using a synthetic aperture analysis technique to obtain a focused image of at least a region of the wind turbine blade based on the reflected microwave signals.

20 Claims, 9 Drawing Sheets

SYSTEM AND METHOD FOR INSPECTING A WIND TURBINE BLADE

BACKGROUND

The invention relates generally to wind turbines and more particularly to a system and method of inspecting a wind turbine blade.

Wind turbines generate electricity from the kinetic energy of wind. Each wind turbine includes three major components: a structural support component, a generator component, and a rotor component. The rotor component further includes wind turbine blades that are employed to convert the kinetic energy of wind to mechanical energy which is then converted to electricity by the generator component.

Inspection of wind turbine blades is important for ongoing operation of wind turbines. One method to inspect a wind turbine blade includes using an ultrasound probe to scan the surfaces of the wind turbine blade. The use of the probe on the surfaces of the wind turbine blade to measure defects is a complex scanning process since the probe needs to follow the surface contour of the wind turbine blade and a couplant is required for ultrasound measurement of the wind turbine blade. Moreover, each surface needs to be inspected separately, resulting in more inspection time and costs.

Therefore, there is a need for an improved wind turbine blade inspection system.

BRIEF DESCRIPTION

In accordance with one embodiment disclosed herein, a wind turbine blade inspection system comprises a frequency modulated continuous wave radar system configured to be movable with respect to a wind turbine blade while transmitting reference microwave signals and receiving reflected microwave signals and a processor configured for using a synthetic aperture analysis technique to obtain a focused image of at least a region of the wind turbine blade based on the reflected microwave signals.

In accordance with another embodiment, a method for inspecting a wind turbine blade comprises: using an inspection system for transmitting reference microwave signals towards the wind turbine blade and receiving reflected microwave signals from the wind turbine blade while moving the inspection system with respect to the wind turbine blade; and obtaining a focused image of at least a region of the wind turbine blade based on the reflected microwave signals using a synthetic aperture analysis technique.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the present invention include a wind turbine blade inspection system. The wind turbine blade inspection system includes a frequency modulated continuous wave (FMCW) radar system and a processor. The FMCW radar system is configured to be movable with respect to a wind turbine blade while transmitting reference microwave signals and receiving reflected microwave signals. The FMCW radar system may be movable by being situated within a movable housing. Additionally or alternatively, the FMCW radar system may itself be movable within a housing. In one embodiment, FMCW radar system is moved in at least a vertical direction as the wind turbine blade rotates while transmitting the reference microwave signals and receiving the reflected microwave signals. In another embodiment which is particularly useful while inspecting a stationary wind turbine blade, the FMCW radar system is moved in at least two directions (via physical movement of a housing and/or changing a directional angle of the inspection system within the housing, for example) while transmitting the reference microwave signals and receiving the reflected microwave signals. The processor may be situated either at the location of the FMCW radar system or remotely and is configured for using a synthetic aperture analysis technique to obtain a focused image of at least a region of the wind turbine blade based on the reflected microwave signals. As used herein, the terms "a" and "an" do not denote a limitation of quantity, but rather denote the presence of at least one of the referenced item.

Figure 1:
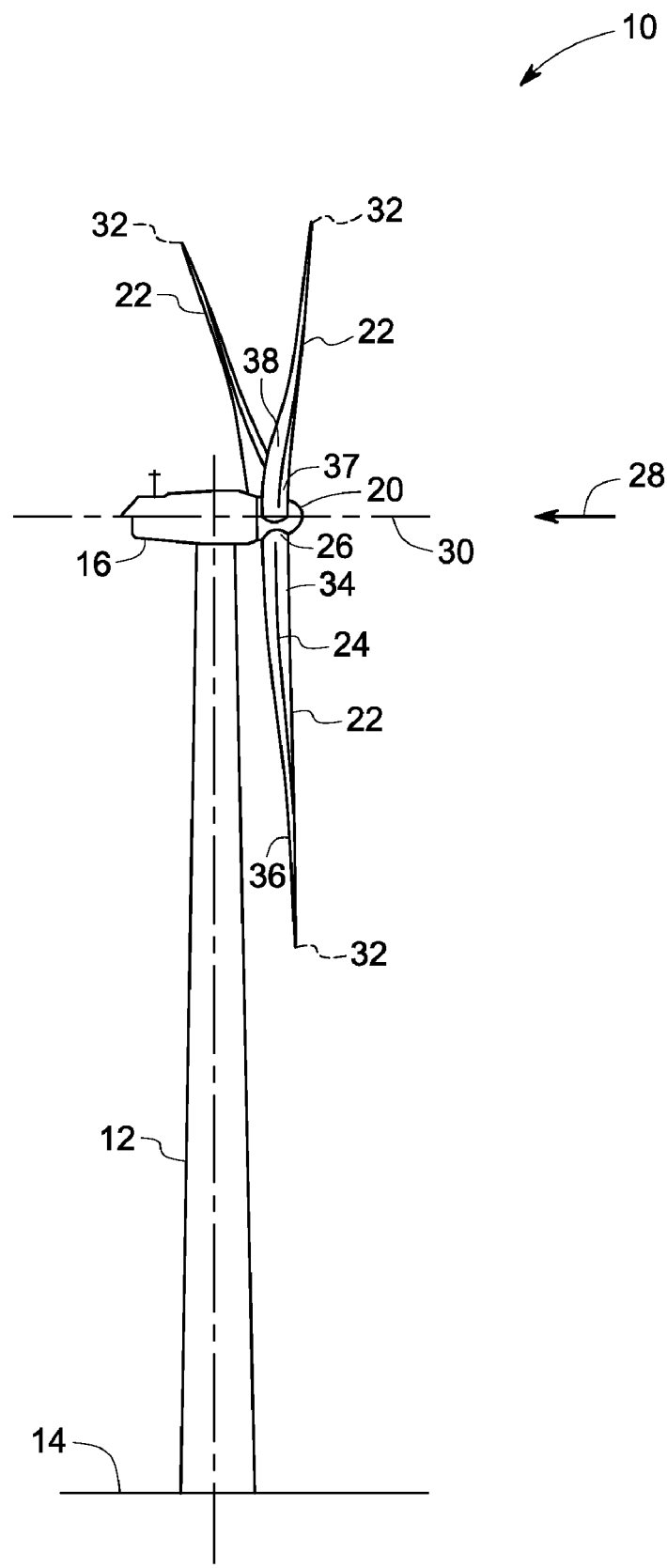
FIG. 1 is a schematic representation of a wind turbine.

FIG. 1 is a schematic representation of a wind turbine 10. The wind turbine 10 includes a tower 12 that extends from a support system 14, a nacelle 16 mounted on the tower 12, and a rotor 18 that is coupled to the nacelle 16. The rotor 18 includes a rotatable hub 20 and at least one wind turbine blade 22 coupled to and extending outward from hub 20. In an exemplary embodiment, the rotor 18 has three wind turbine blades 22. The wind turbine blades 22 are mated to the hub 20 by coupling the wind turbine blades 22 to the hub 20 at a plurality of roots 26. Loads induced to the wind turbine blades 22 are transferred to the hub 20 via the plurality of roots 26. In one embodiment, the wind turbine blades 22 have a length ranging from about 15 meters (m) to about 91 m.

The wind strikes the wind turbine blade 22 from a direction 28 that causes the rotor 18 to rotate about an axis of rotation 30. The wind turbine blade 22 includes a tip 32. An edge of the wind turbine blade 22 that faces the wind and is a front edge along the direction of rotation 30 of the wind turbine blade 22 is known as the leading edge 34, and an edge of the wind turbine blade that follows the leading edge is known as the trailing edge 36. A surface of the wind turbine blade 22 at higher pressures (primarily facing the wind 28) is known as a pressure side 37, and a surface of the wind turbine blade 22 exposed to lower pressures is known as a suction side 38. The wind turbine blades 22 are subject to damage during operation due to wear and tear from normal operating conditions as well as damage due to unusual environmental conditions.

Figure 2:
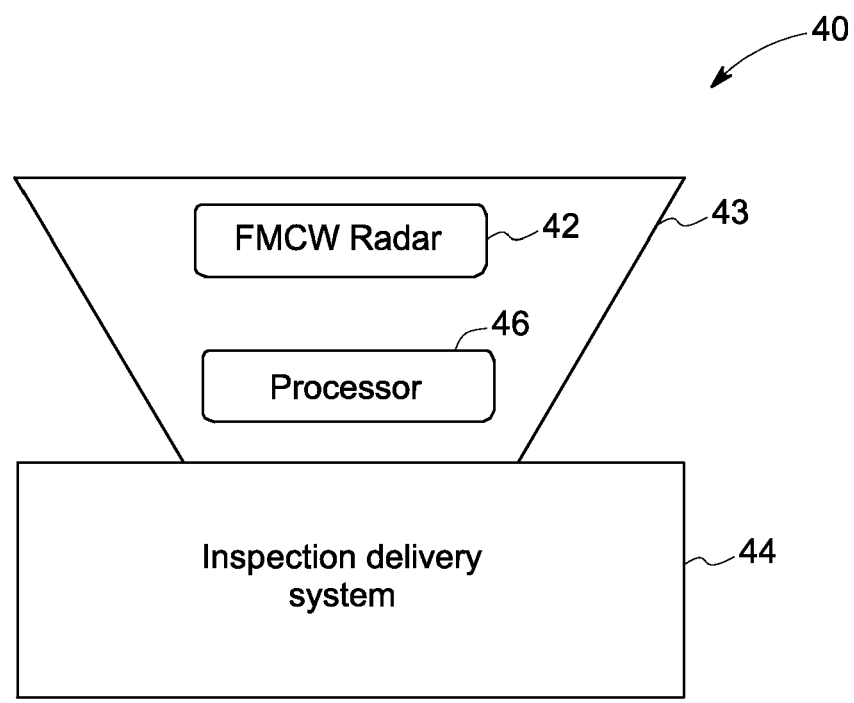
FIG. 2 is a block diagram representation of a wind turbine blade inspection system including a microwave inspection system in accordance with an embodiment of the invention.

FIG. 2 is a block diagram representation of a wind turbine blade inspection system 40 for inspection of the wind turbine blade of FIG. 1 in accordance with an embodiment of the invention. The wind turbine blade inspection system 40 includes a microwave inspection system 42. The microwave inspection system 42 is configured to be movable while transmitting the reference microwave signals and receiving the reflected microwave signals. The microwave inspection system 42 is mounted on in a housing which is depicted as inspection delivery system 44. Exemplary embodiments of inspection delivery systems 44 include a tower crawler, an aerial vehicle, and a ground based system. The microwave inspection system 42 includes a frequency modulated continuous wave (FMCW) radar system 46 configured to transmit reference microwave signals towards the wind turbine blade (FIG. 1) over a wide frequency bandwidth. Any desired bandwidth capable of providing the desired resolution may be used with higher bandwidths being useful for providing higher resolution. The desired resolution and the related bandwidth to obtain that resolution are dependent at least in part on the specific material of the wind turbine blade. In one embodiment for a wind turbine blade comprising fiberglass material, for example, the frequency bandwidth may comprise at least 7 GHz which may start at any desired frequency. In a more specific embodiment, a frequency bandwidth of 20 GHz is used. The FMCW radar system 46 transmits continuous waves toward the rotating wind turbine blade while sweeping the frequency of the continuous waves over the frequency bandwidth. The transmitted continuous waves are reflected back from the wind turbine blade and are received by the FMCW radar system 46. By ensuring that there is a relative motion between the FMCW radar system 46 and the wind turbine blade (FIG. 1), synthetic aperture focusing algorithms can be employed to improve spatial resolution of the images.

Generally, synthetic-aperture radar (SAR) techniques are based on the fact that a relative motion between an inspection system and its target provides distinctive coherent-signal variations that may be exploited to obtain finer spatial resolution than is possible with conventional beam-scanning means. The waveforms received successively at the different inspection positions may be coherently detected, stored, and later post-processed together to resolve elements in an image of the target region. In a radar system including a microwave antenna, for example, the SAR spatial resolution is related to the aperture size of the microwave antenna by the following equation (equation 1) $\delta_{xy} = \lambda_c/4 \sin(\theta_b/2)$, wherein $\lambda_c$ is the wavelength at the central FMCW radar frequency and beam width angle $\theta_b = \lambda_c/D$ wherein D is the antenna aperture. Furthermore, a depth resolution is determined by the bandwidth (B) of the FMCW radar system and the dielectric constant $\in$ of the material of the wind turbine blade as shown by the following equation (equation 2) $\delta_z = c/2B\sqrt{\in}$, wherein c is the velocity of light in vacuum. This technique enables creation of a three-dimensional image and thus sometimes is also referred to as "holographic SAR imaging" in radar literature.

Figure 3:
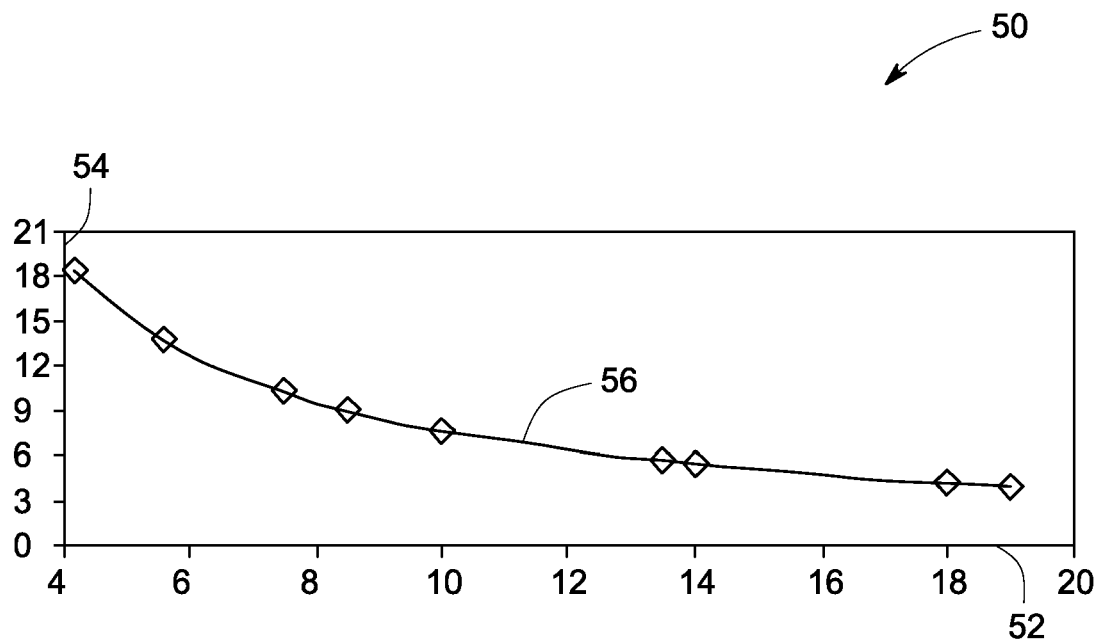
FIG. 3 is a graphical illustration of a model of variation of a depth resolution in a fiber glass relative to a bandwidth of the frequency modulated continuous wave radar signals transmitted to a wind turbine blade of FIG. 1 in accordance with an embodiment of the invention.

FIG. 3 is a graphical illustration 50 of a model of variation of the depth resolution in fiberglass material relative to the bandwidth of the FMCW radar signals transmitted to the fiberglass material. The X-axis 52 represents the bandwidth of the FMCW radar system in Gigahertz. The Y-axis 54 represents a depth resolution in the fiberglass in millimeters. The curve 56 represents variation of the depth resolution relative to the bandwidth of the reference microwave signals. As observed, the depth resolution decreases from about 18 mm to 4 mm with an increase in the bandwidth of the reference microwave signals respectively.

Figure 4:
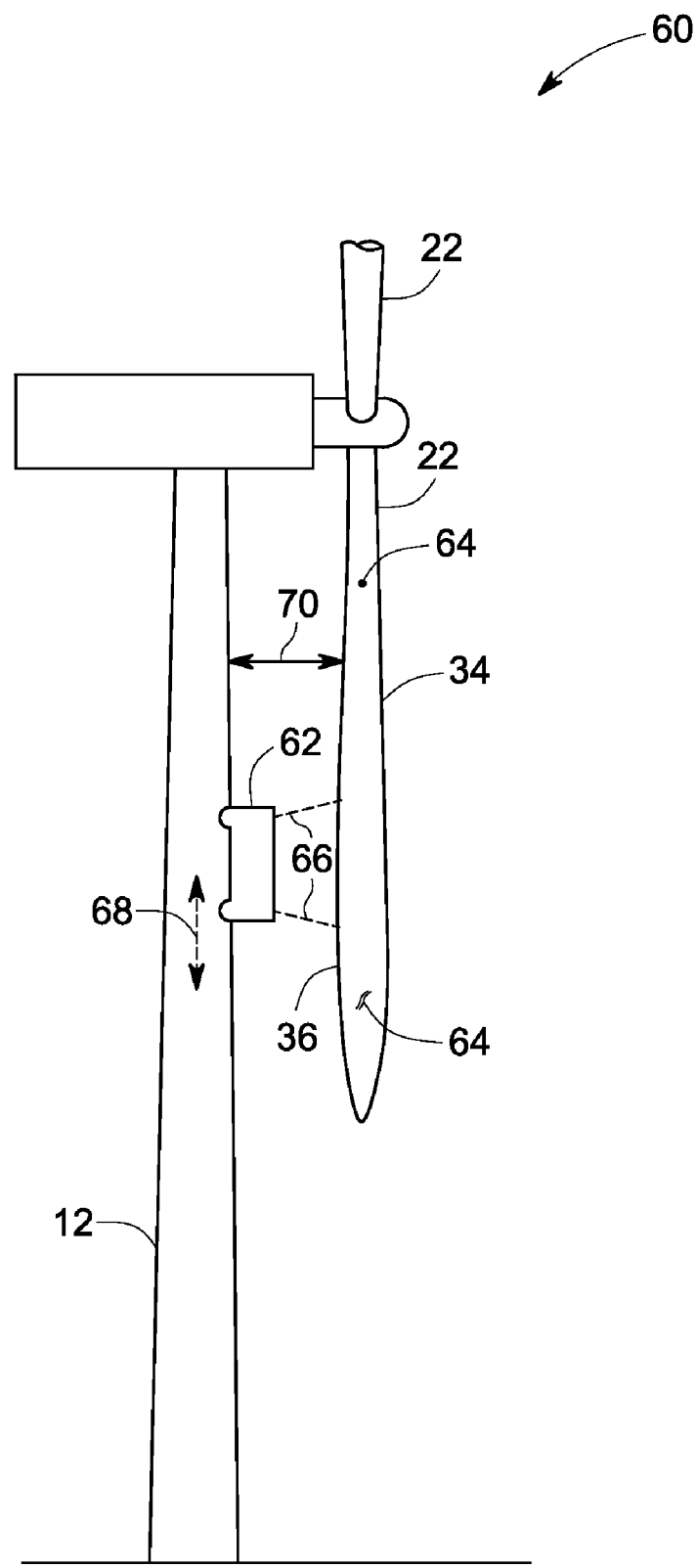
FIG. 4 is a schematic representation of a wind turbine blade inspection system including a tower crawler mounted with the microwave inspection system of FIG. 2 in accordance with an embodiment of the invention.

FIG. 4 is a schematic representation of a wind turbine blade inspection system 60 including a tower crawler 62 mounted with the microwave inspection system 42 of FIG. 2 in accordance with an embodiment of the invention. The tower crawler 62 moves up and down the tower 12 of the wind turbine and reaches a height equivalent to the wind turbine blade 22. In one embodiment the tower crawler 62 may be attached to a tensile rope (not shown) to assist the tower crawler 62 to crawl along the tower 12 of the wind turbine as described in commonly assigned U.S. patent application Ser. No. 12/823,525 filed on Jun. 25, 2010.

While at height on the wind turbine tower where the tower crawler 62 is facing the wind turbine blade 22, the FMCW radar system (FIG. 2) transmits the reference microwave signals 66 towards the rotating wind turbine blade 22 and moves in a vertical direction 68 along the tower 12 of the wind turbine. In the tower crawler embodiment, mechanical constraints on the distance between the tower and tower crawler 62 may affect how close the FMCW radar system may be positioned with respect to the blade. In an exemplary embodiment, the standoff distance 70 between the tower crawler 62 and the wind turbine blade 22 can vary and be as close as 2 meters to as far as 10 meters, for example. Furthermore, simultaneously rotating the wind turbine blade 22 and moving the FMCW radar system in a vertical direction with respect to the wind turbine blade 22 enables the microwave inspection system (FIG. 2) to obtain spiral scans (FIG. 5) of the wind turbine blade. The spiral scans are used by the processor for simultaneously inspecting both the pressure side (FIG. 1) and the suction side (FIG. 1) of the wind turbine blade for potential surface and sub surface defects 64. Furthermore, the spiral scans are processed using synthetic aperture analysis technique to obtain a focused image (such as an image of the type shown in FIG. 11) of at least a region of the wind turbine blade 22 based on the reflected microwave signals. The microwave inspection system is continuously moved to obtain an image of the whole wind turbine blade 22 via repeating the above mentioned steps. In some embodiments, to obtain a better view of edges of the wind turbine blade, selective pitching of the wind turbine blades may be used during the inspection process. A choice of an appropriate pitch angle may also be useful to provide for better inspection (and access for inspection) of more complicated structural locations within the blade in some embodiments.

Figure 5:
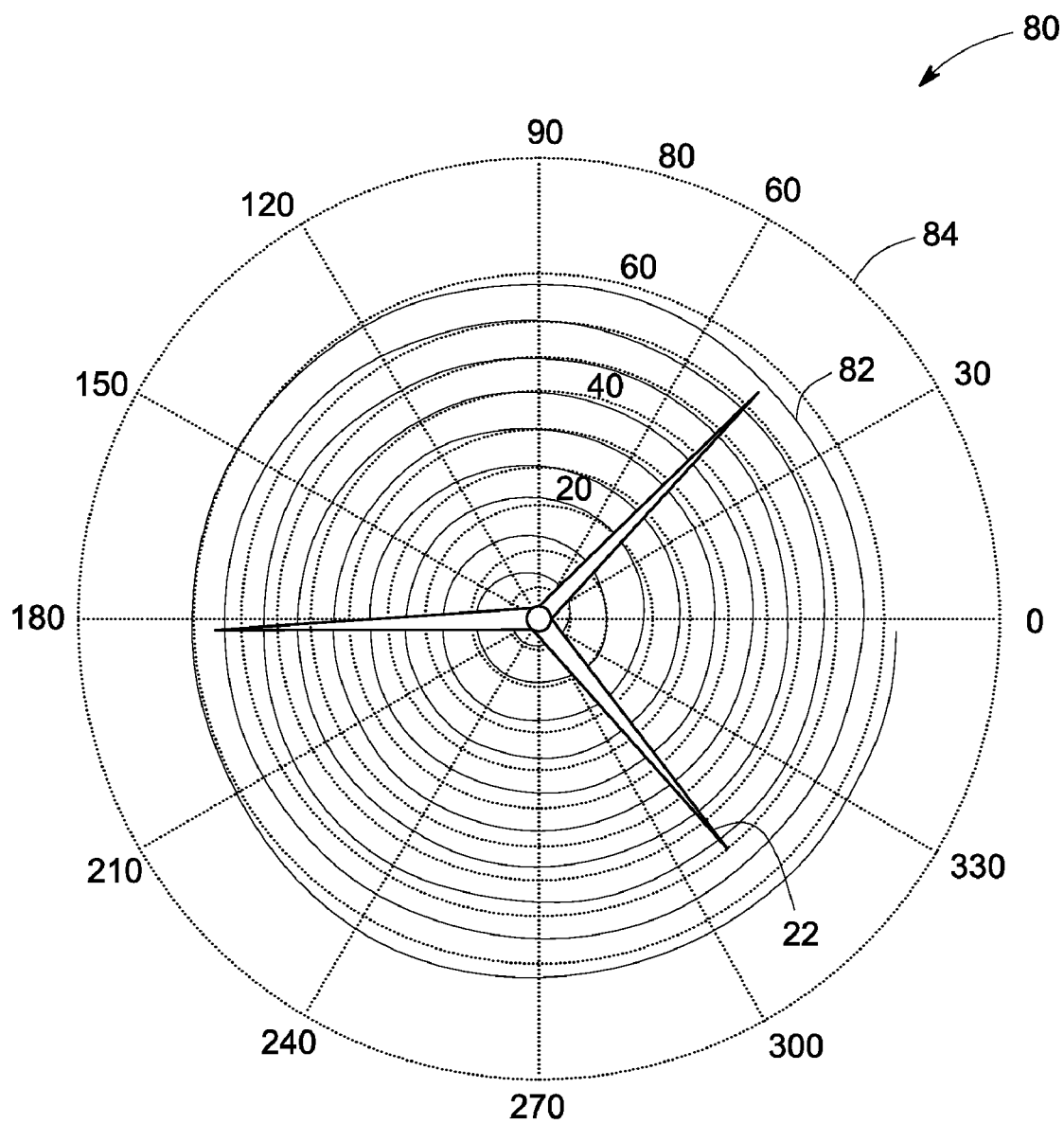
FIG. 5 is a schematic representation of a model of a spiral scan of the microwave inspection system of FIG. 2 in accordance with an embodiment of the invention.

FIG. 5 is a schematic representation of a model of a spiral scan 80 of the microwave inspection system of FIG. 2 in accordance with an embodiment of the invention. As shown, the microwave inspection system is configured to scan the wind turbine blade 22 via a path 82 traversed by the FMCW radar system in a reference frame 84 of the wind turbine blade 22.

Figure 6:
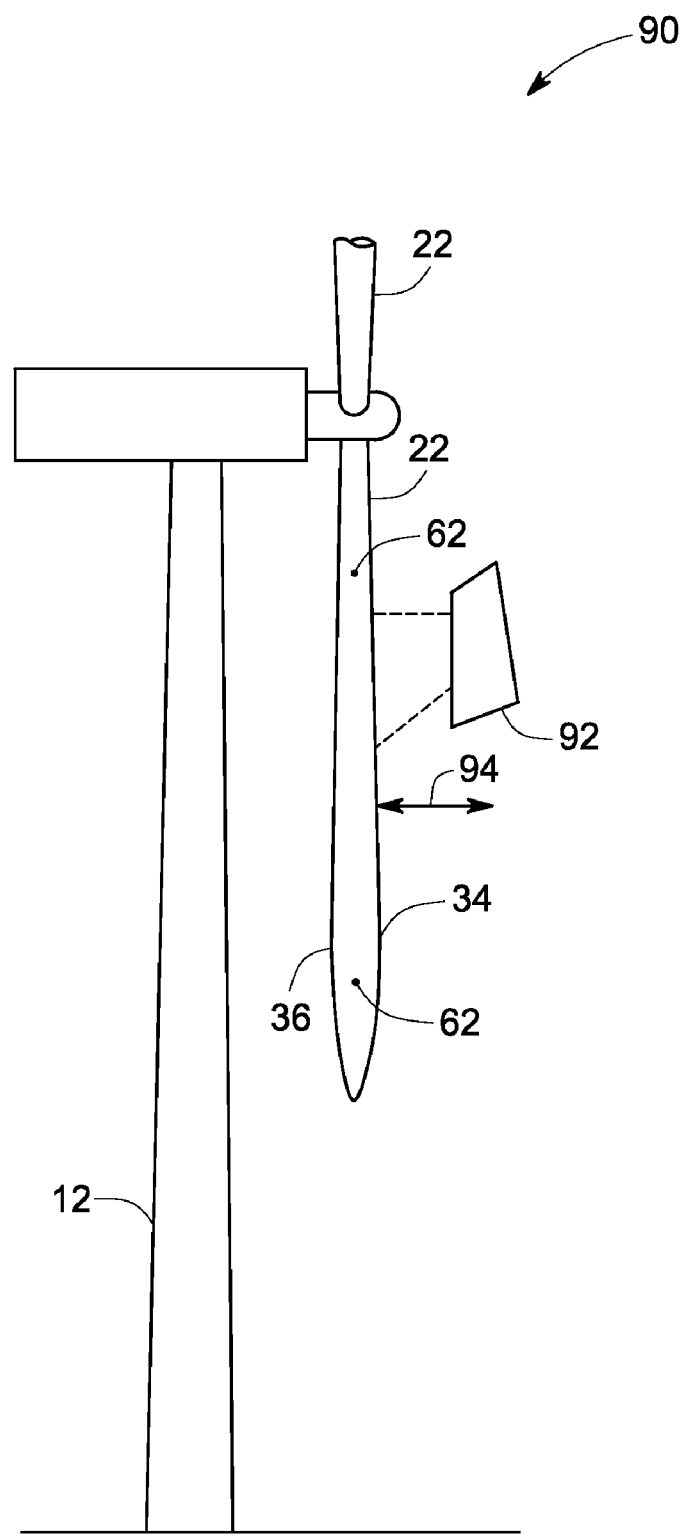
FIG. 6 is a schematic illustration of a wind turbine blade inspection system including the microwave inspection system of FIG. 2 mounted on an aerial vehicle for inspecting the wind turbine blade in accordance with an exemplary embodiment of the invention.

FIG. 6 is a schematic illustration of a wind turbine blade inspection system 90 including the microwave inspection system 42 of FIG. 2 mounted on an aerial vehicle 92 for inspecting the wind turbine blade 22 in accordance with an exemplary embodiment of the invention. The aerial vehicle 92 is remotely controlled to reach the wind turbine blade 22 at a standoff distance 94 from the wind turbine blade 22 and be movable in a vertical direction along the wind turbine blade 22 to inspect the wind turbine blade 22 for defects 64 with the microwave inspection system (FIG. 2) as described above with respect to FIG. 3. There is more flexibility in the aerial vehicle 92 embodiment with respect to the standoff distance 94. The standoff distance 94 is programmable to be any value that allows acquisition of optimum radar data without interfering or colliding with the wind turbine blade 22. Standoff distances 94 will typically, but not necessarily, be in the range from 10 cm to 10 m.

In one version of the aerial vehicle embodiment, the blade rotates while the aerial vehicle moves at least in a vertical direction to obtain spiral scans of the type discussed above. If desired in the wind blade rotating embodiment, in addition to moving in a vertical direction, the aerial vehicle may also move horizontally to more easily catch data from the edges of the wind blade and/or the blades may be selectively pitched as discussed above. In another version of the aerial vehicle embodiment, the wind blade does not need to rotate, and the aerial vehicle is moved in at least two directions (such as, for example, in a spiral path or in vertical and horizontal directions) while transmitting the reference microwave signals and receiving the reflected microwave signals.

Figure 7:
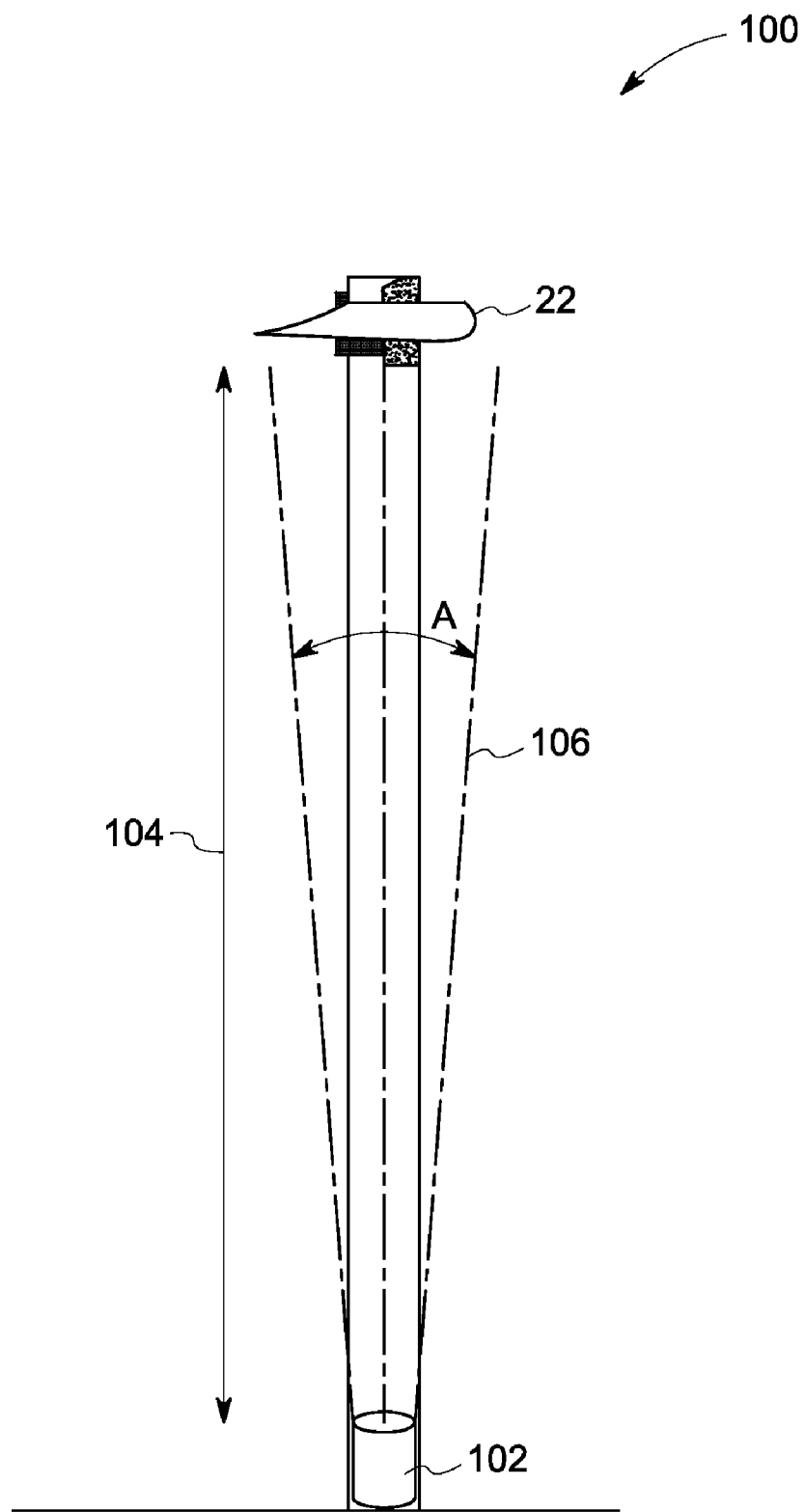
FIG. 7 and FIG. 8 are schematic representations of a ground based wind turbine blade inspection system configured to inspect the wind turbine blade in accordance with yet another embodiment of the invention.
Figure 8:
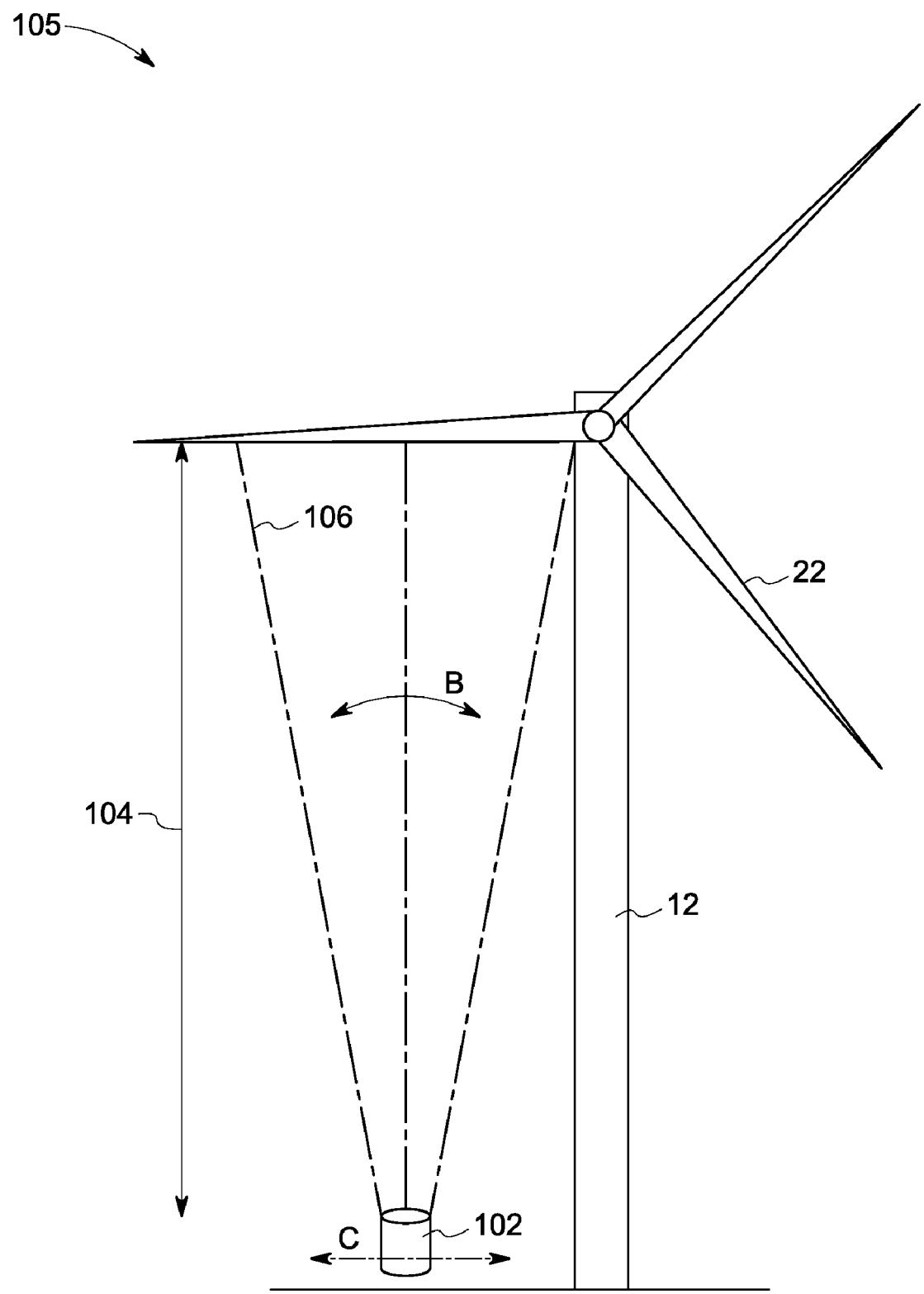

FIG. 7 and FIG. 8 are schematic representations 100 and 105 respectively of a ground based inspection system 102 configured to inspect the wind turbine blade 22 in accordance with yet another embodiment of the invention. In one ground based embodiment, the FMCW radar system (FIG. 2) is mounted on a stationary ground based inspection system 102 configured for continuous multi-axis tilting (as shown by axes A and B) during the inspection process. In another ground based embodiment, the ground based inspection system 102 may be movable on the ground in one direction (such as shown by direction C) and tilted in another direction (such as shown by direction B). In another ground based embodiment, the ground based inspection system 102 is moved in at least two directions and no tilting is required. Blade pitching may additionally be used in any of these embodiments if desired.

In ground based embodiments, the wind turbine blades 22 may be sequentially moved to 9 o'clock or 3 o'clock positions and optionally pitched at various angles (most common being at 90 degrees, but other angles could help with inspection of the leading edge 34 or other structural locations) and held steady during the inspection process. Typically the standoff distance 104 in ground based embodiments will be longer than either of the other embodiments and in one example is about the height of the wind turbine tower 12, which is typically anywhere from 80 m to 120 m tall. Obtaining sufficient resolution and accuracy can be more of a challenge in ground based embodiments. In one embodiment, the microwave power for the reference signals 106 is higher than the microwave power that would be used to inspect the wind turbine blades in the tower crawler and aerial vehicle embodiments. In one specific embodiment to increase resolution, the microwave inspection system (FIG. 2) includes a pan-tilt-zoom microwave antenna that includes a wide band adaptive dielectric lens configured to zoom on the wind turbine blade 22 to provide better collimation and focusing of the microwave energy at the wind turbine blade 22. If desired, this type of antenna may be used in the tower crawler and aerial vehicle embodiments as well.

Figure 9:
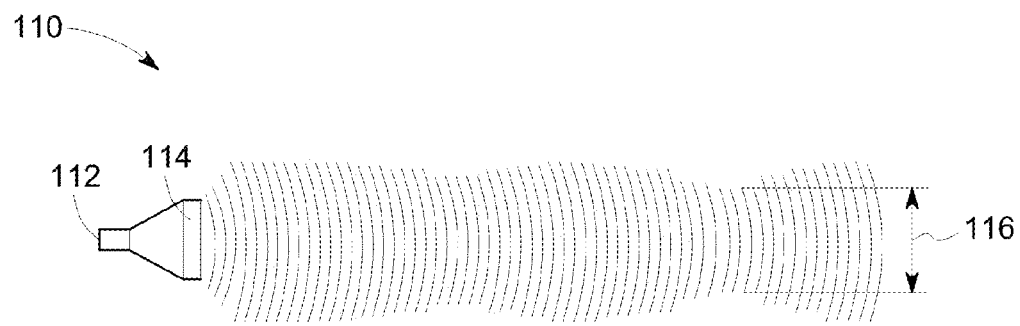
FIG. 9 is a schematic representation of the pan-tilt-zoom microwave antenna including the wide band adaptive dielectric lens for collimating and focusing of reference microwave signals at the wind turbine blade in accordance with an embodiment of the invention.

FIG. 9 is a schematic representation 110 of the pan-tilt-zoom microwave antenna 112 including the wide band adaptive dielectric lens 114 for collimating and focusing of reference microwave signals at the wind turbine blade in accordance with an embodiment of the invention. The wide band adaptive dielectric lens 114 directs most of the microwave energy to a small region 116 of the wind turbine blade (FIG. 1) that is particularly useful in a case where larger standoff distances are required. The wide band adaptive dielectric lens 114 focuses and collimates the microwave energy to realize the zoom function of the pan-tilt-zoom microwave antenna 112. Furthermore, the pan-tilt function is provided by tilting or rotating the antennas of the pan-tilt-zoom microwave antenna 112.

A method for inspecting a wind turbine blade is also provided. The method includes transmitting reference microwave signals towards the wind turbine blade while moving an inspection system with respect to the wind turbine blade. The method also includes receiving reflected microwave signals from the wind turbine blade while moving the inspection system with respect to the wind turbine blade. In an embodiment, the inspection system is moved in at least a vertical direction as the wind turbine blade rotates while transmitting the reference microwave signals and receiving the reflected microwave signals. In another embodiment the inspection system is moved in at least two directions as the wind turbine blade is stationary while transmitting the reference microwave signals and receiving the reflected microwave signals. In a particular embodiment, transmitting the reference microwave signals include transmitting the reference microwave signals from a standoff distance of about 2 meters to about 10 meters. The method further includes obtaining a focused image of at least a region of the wind turbine blade based on the reference microwave signals and reflected microwave signals using a synthetic aperture analysis technique. In one embodiment the focused image is obtained by simultaneously inspecting both a pressure side and a suction side of the wind turbine blade. The pressure side and the suction side are inspected for surface and sub surface defects. The inspection of surface and subsurface defects may include detecting voids, disbonds and delaminations in the wind turbine blade. In one embodiment, the pressure side and the suction side are inspected for surface and subsurface defects by collecting multiple spiral scans of the wind turbine blade. The multiple spiral scans generate the focused image. In an embodiment the focused image is a three dimensional image.

EXAMPLES

Figure 10:
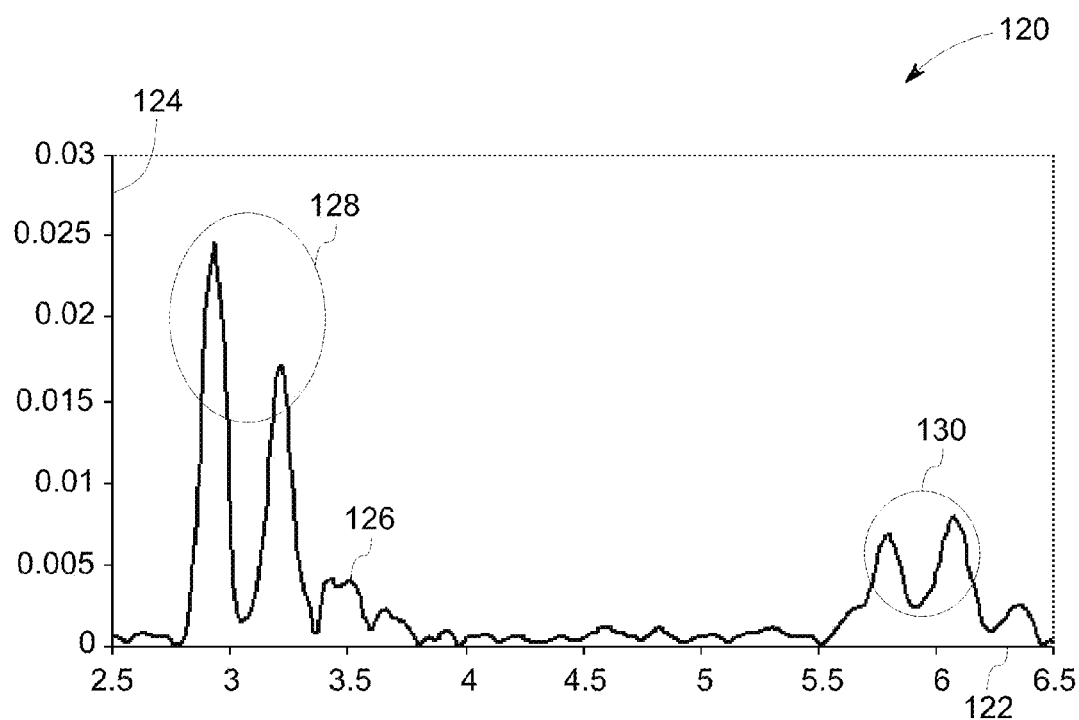
FIG. 10 is a graphical representation of frequency modulated continuous wave radar data collected from a measurement depicting features that can be attributed to a higher pressure side (pressure side) and a lower pressure side (suction side) of the wind turbine blade in accordance with an embodiment of the invention.

FIG. 10 is a graphical representation of FMCW radar data collected from a measurement depicting features that can be attributed to the pressure side and the suction side of the wind turbine blade (FIG. 1) in accordance with an embodiment of the invention. The FMCW radar data was collected from a single measurement in a lab scale test wherein a wind blade segment was kept stationary and an antenna was moved along the span and chord of the wind turbine blade segment. The single measurement depicts features that can be attributed to the pressure side and the suction side of the wind turbine blade. The X-axis 122 represents the time of flight of the microwave energy in nanoseconds. The Y-axis 124 represents the reflection coefficient of the microwave energy. The curve 126 represents variation of the reflected microwave energy as a function of travel time. This travel time, or time of flight, can be converted to the distance between the microwave inspection system and the wind turbine blade features by using the velocity of light in air and in various materials through which the microwaves may travel. The distance represents the depth or range information. Thus the region 128 of curve 126 can be attributed to the portion of the blade closest to the antenna whereas region 130 of the curve 126 can be attributed to the portion of blade farthest from the antenna. When the microwave inspection system is situated on the tower (FIG. 4), the closest region will likely be situated on the suction side (FIG. 1) of the wind turbine blade, whereas when the microwave inspection system is in an aerial embodiment (FIG. 6), the closest region is more likely to be on the pressure side (FIG. 1) of the wind turbine blade, for example.

Figure 11:
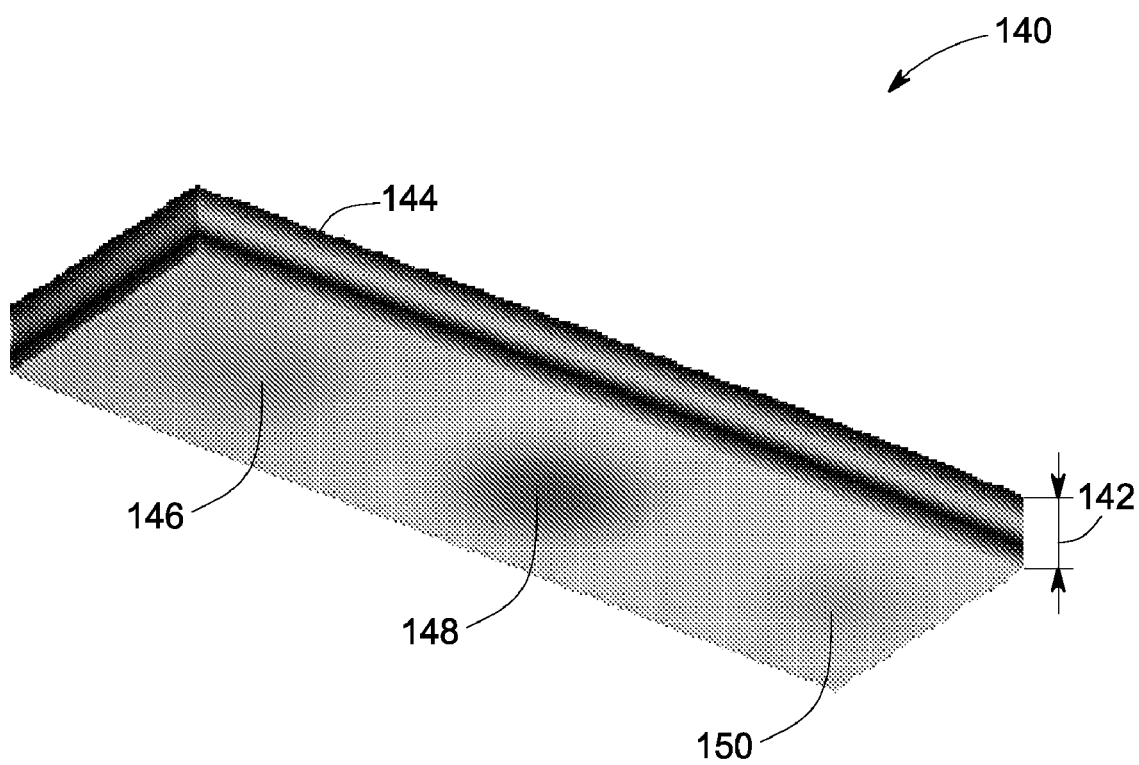
FIG. 11 is a schematic representation of a three dimensional image generated in accordance with an embodiment of the invention.

FIG. 11 is a schematic representation of a three dimensional image 140 generated by the wind turbine blade inspection system of a fiberglass plate 142 with known defects in accordance with an embodiment of the invention. The wind turbine blade inspection system includes an antenna that was moved to a plurality of locations along a length and a width of one side 144 of the fiberglass plate 142 having a thickness of 12 millimeters. The spatial information thus collected was used to generate the three-dimensional image 140. More specifically, the microwave inspection system was used to generate a plurality of two dimensional B-scan and C-scan images which were then used to generate the three dimensional image 140. The three dimensional image 140 includes the surface and the sub surface defects in the wind turbine blade with the subsurface defects being illustrated by 146, 148 and 150 having diameters of 75 mm, 125 mm and 50 mm respectively.

The various embodiments of the inspection system and method for inspecting a wind turbine blade described above are useful and cost effective as these embodiments do not require the wind blade to be taken out of service and do not require the use of a couplant.

The skilled artisan will recognize the interchangeability of various features from different embodiments. For example, a pan-tilt-zoom microwave antenna with respect to one embodiment can be adapted for use with respect to another embodiment of the invention to provide an inspection system to inspect the wind turbine blade. Similarly, the various features described, as well as other known equivalents for each feature, may be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A wind turbine blade inspection system comprising:
   a frequency modulated continuous wave radar system configured to be movable with respect to a wind turbine blade while transmitting reference microwave signals and receiving reflected microwave signals; and
   a processor configured for using a synthetic aperture analysis technique to obtain a focused image of at least a region of the wind turbine blade based on the reflected microwave signals.

2. The wind turbine blade inspection system of claim 1, wherein the frequency modulated continuous wave radar system is configured to be movable in at least a vertical direction as the wind turbine blade rotates while transmitting the reference microwave signals and receiving the reflected microwave signals.

3. The wind turbine blade inspection system of claim 2, wherein the frequency modulated continuous wave radar system is embodied in a wind turbine tower crawler.

4. The wind turbine blade inspection system of claim 1, wherein the frequency modulated continuous wave radar system is configured to be movable in at least two directions as the wind turbine blade is stationary while transmitting the reference microwave signals and receiving the reflected microwave signals.

5. The wind turbine blade inspection system of claim 4 wherein the frequency modulated continuous wave radar system is embodied in a ground based inspection system.

6. The wind turbine blade inspection system of claim 1, wherein the frequency modulated continuous wave radar system is embodied in an aerial vehicle.

7. The wind turbine blade inspection system of claim 1, wherein the frequency modulated continuous wave radar system comprises a pan-tilt-zoom microwave antenna.

8. The wind turbine blade inspection system of claim 7, wherein the pan-tilt-zoom microwave antenna comprises a wide band low loss adaptive dielectric lens.

9. The wind turbine blade inspection system of claim 1, wherein the processor generates a three dimensional image.

10. The wind turbine blade inspection system of claim 1, wherein the wind turbine blade inspection system is capable of simultaneously inspecting both a pressure side and a suction side of the wind turbine blade for surface and subsurface defects.

11. The wind turbine blade of claim 10, wherein the surface and the subsurface defects include voids, disbonds, and delaminations.

12. The wind turbine blade inspection system of claim 1, wherein a frequency bandwidth of the frequency modulated continuous wave radar system comprises a bandwidth of at least seven gigahertz.

13. A method for inspecting a wind turbine blade comprising:
   using an inspection system for transmitting reference microwave signals towards the wind turbine blade and receiving reflected microwave signals from the wind turbine blade while moving the inspection system with respect to the wind turbine blade;
   obtaining a focused image of at least a region of the wind turbine blade based on the reflected microwave signals using a synthetic aperture analysis technique.

14. The method of claim 13, wherein moving the inspection system comprises moving the inspection system in at least a vertical direction as the wind turbine blade rotates while transmitting the reference microwave signals and receiving the reflected microwave signals.

15. The method of claim 13, wherein moving the inspection system comprises moving the inspection system in at least two directions as the wind turbine blade is stationary while transmitting the reference microwave signals and receiving the reflected microwave signals.

16. The method of claim 13, wherein transmitting the reference microwave signals comprises transmitting the reference microwave signals from a standoff distance of about 2 meters to about 10 meters.

17. The method of claim 13, wherein obtaining the artificially focused image comprises obtaining a plurality of spiral scans of the wind turbine blade.

18. The method of claim 13, wherein obtaining the artificially focused image comprises simultaneously inspecting both a pressure side and a suction side of the wind turbine blade.

19. The method of claim 18, wherein inspecting both the pressure side and the suction side of the wind turbine blade comprises inspecting surface and sub surface defects.

20. The method of claim 13, wherein obtaining the focused image comprises obtaining a three dimensional image of the wind turbine blade.

* * * * *

UNITED STATES PATENT AND TRADEMARK OFFICE
Certificate

Patent No. 8,120,522 B2                                                                        Patented: February 21, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nilesh Tralshawala, Rexford, NY (US); Waseem Ibrahim Faidi, Schenectady, NY (US); Reza Zoughi, Wildwood, MO (US); and Sergiy Kharkivskiy, Penrith (AU).

Signed and Sealed this Nineteenth Day of August 2014.

*JACK W. KEITH*
*Supervisory Patent Examiner*
*Art Unit 3646*
*Technology Center 3600*